United States Patent
Itsykson (10) Patent No.: US 10,412,959 B2
(45) Date of Patent: Sep. 17, 2019

(54) CELL TRAY

(71) Applicant: MFC GLOBAL LTD, Givat Shmuel (IL)

(72) Inventor: Pavel Itsykson, Bat Yam (IL)

(73) Assignee: ASSUTA MEDICAL CENTERS LTD., Tel Aviv (IL)

( * ) Notice: Subject to any disclaimer, the term of this patent is extended or adjusted under 35 U.S.C. 154(b) by 116 days.

(21) Appl. No.: 15/310,381

(22) PCT Filed: May 11, 2015

(86) PCT No.: PCT/IL2015/050495
§ 371 (c)(1),
(2) Date: Nov. 10, 2016

(87) PCT Pub. No.: WO2015/173809
PCT Pub. Date: Nov. 19, 2015

(65) Prior Publication Data
US 2017/0238534 A1    Aug. 24, 2017

Related U.S. Application Data

(60) Provisional application No. 61/992,484, filed on May 13, 2014.

(51) Int. Cl.
*A01N 1/02* (2006.01)
*A61B 17/43* (2006.01)
*A61D 19/02* (2006.01)

(52) U.S. Cl.
CPC ............ *A01N 1/0268* (2013.01); *A61B 17/43* (2013.01); *A61D 19/022* (2013.01)

(58) Field of Classification Search
CPC ..... A01N 1/0268; A61B 17/43; A61D 19/022
See application file for complete search history.

(56) References Cited

U.S. PATENT DOCUMENTS 5,044,500 A * 9/1991 Webber et al. ........ G02B 21/34
                                                        206/455
5,292,000 A * 3/1994 Levy .................. A61B 10/0096
                                                        206/456

(Continued)

FOREIGN PATENT DOCUMENTS

JP       2007302256 A       11/2007
WO    WO2006/059626    *  6/2006
WO    WO 2006/059626 A1    6/2006

OTHER PUBLICATIONS

European Office Action dated May 22, 2018.

(Continued)

*Primary Examiner* — Gautam Prakash
(74) *Attorney, Agent, or Firm* — Symbus Law Group, LLC; Clifford D. Hyra (57) ABSTRACT

An apparatus is provided for use with a fluid that contains biological cells, e.g. seminal fluid. The apparatus (20) includes a tray (22) shaped to define a flat upper surface configured to support the fluid, and an underside. The apparatus (20) further includes a plurality of protrusions protruding from the underside of the tray, which may serve to separate the underside from a flat surface on which the tray is placed, or as delineating protrusions that facilitate subsequent retrieval of the fluid following placement on the tray. The tray has a thickness between 0.4 and 0.8 mm, and is transparent or translucent. The upper surface preferably has a level of hydrophobicity that is sufficient for droplets to maintain their shape to a certain extent. A handle (52) facilitates handling of the tray. The apparatus typically fits into a standard-sized cryogenic vial (70).

13 Claims, 6 Drawing Sheets

(56) References Cited

U.S. PATENT DOCUMENTS

| | | | | |
|---|---|---|---|---|
| 7,147,826 | B2* | 12/2006 | Haywood et al. | B01L 3/502 422/547 |
| 2010/0184127 | A1* | 7/2010 | Williamson, IV et al. | G01N 1/06 435/40.52 |
| 2014/0157798 | A1* | 6/2014 | Jimenez-Rios | A01N 1/0257 62/62 |

OTHER PUBLICATIONS

Zou, et al. "On-Chip Cryopreservation: A Novel Method for Ultra-Rapid Cryoprotectant-Free Cryopreservation of Small Amounts of Human Spermatozoa," Apr. 30, 2013 DOI: 10.1371/journal.pone.0061593.

Eshre 2007, 23rd Annual Meeting, "Artificial microcontainers for cryopreservation of solitary spermatozoa," Jul. 1-5, 2007, Lyon, pp. 1-4.

AbdelHafez, et al., "Techniques for cryopreservation of individual or small numbers of human spermatozoa: a systematic review," Human Reproduction Update, vol. 15, No. 2 pp. 153-164, 2009; Advanced Access publication on Dec. 24, 2008 doi:10.1093/humupd/dmn061.

Mears, et al. "Reduced curvilinear velocity of boar sperm on substrates with increased hydrophobicity," Theriogenology 81 (2014) 764-769.

Endo et al., "Single Spermatozoon Freezing Using Cryotop," Journal of Mammalian Ova Research/Apr. 2011/ p. 4752.

Endo et al., "Simple vitrification for small numbers of human spermatozoa," Reproductive BioMedicine Online (2012) 24, 301-307.

Li et al., "OnChip Cryopreservation of Living Cells," Journal of Laboratory Automation Apr. 2010 vol. 15 No. 2 99106.

MLO Staff "Surface modified slides let IHC laboratories do more with less," http://www.mlo-online.com/surface-modified-slides-let-ihc-laborat, (pp. 1-4).

Desai, "Single sperm cryopreservation on cryoloops: an alternative to hamster zona for freezing individual spermatozoa," RBM online; vol. 9. No. I. 2004-47-53 Reproductive BioMedicine Online.

Assignment Recorded from MFC Global Ltd. to Assuta Medical Centers Ltd.

* cited by examiner

CELL TRAY

CROSS-REFERENCE TO RELATED APPLICATIONS

The present application claims priority from U.S. Provisional Application 61/992,484, filed May 13, 2014, which is assigned to the assignee of the present application and is incorporated herein by reference.

FIELD OF THE INVENTION

The present invention relates to apparatus and methods for use with fluids that contain biological cells.

BACKGROUND

In some cases, fluid containing biological cells is taken from a subject for purposes of study and/or cryopreservation. For example, in certain techniques related to in-vitro fertilization (IVF), it is desired to cryopreserve seminal fluid taken from a subject.

SUMMARY OF THE INVENTION

Applications of the present invention include apparatus for use with a fluid that contains biological cells, e.g., seminal fluid. The apparatus includes a tray having a flat upper surface configured to support the fluid, and an underside. The upper surface is not completely surrounded by a wall, such that the upper surface is generally more accessible, relative to if it were to be completely surrounded by a wall. The apparatus typically includes a plurality of protrusions protruding from the underside of the tray, including protrusions that support the tray and/or protrusions that delineate portions of the tray for placement thereon of the fluid. Typically, the tray is transparent, e.g., optical grade transparent, or translucent, the transparency or translucency of the tray facilitating placement of fluid on the delineated portions of the tray, and/or extraction of biological cells from the fluid after the fluid has been placed on the tray. The apparatus may be particularly useful for cryogenic storage of seminal fluid that contains only a small number of spermatozoa, even a single spermatozoon. Conventional cryogenic storage techniques are generally ineffective for storing such a small amount of spermatozoa.

Typically, the apparatus further includes a handle having a first handle portion that is generally perpendicular to the tray, and disposed at an end of the tray, and a second handle portion that is generally parallel to the tray, and coupled to the first handle portion. The handle generally facilitates handling of the tray, in that, by virtue of the respective orientations of the first and second handle portions, it may be grasped (e.g., using tweezers) from a number of different directions.

There is therefore provided, in accordance with an application of the present invention, apparatus for use with a fluid that contains biological cells, the apparatus including:

a tray shaped to define:
  a flat upper surface configured to support the fluid, the upper surface not being completely surrounded by a wall and having a surface area that is less than 900 mm2, and
  an underside; and
a plurality of protrusions protruding from the underside of the tray,
the tray having:
  a thickness between 0.4 and 0.8 mm, and
  a property selected from the group consisting of: transparency, and translucency.

For some applications:
  the flat upper surface is shaped to define an outer perimeter,
  at least some of the outer perimeter does not contact any element extending higher than the flat upper surface, and
  at least some of the outer perimeter contacts an element extending higher than the flat upper surface.

For some applications, at least 20% of the outer perimeter does not contact any element extending higher than the flat upper surface. For some applications, at least 40% of the outer perimeter does not contact any element extending higher than the flat upper surface. For some applications, at least 60% of the outer perimeter does not contact any element extending higher than the flat upper surface. For some applications, at least 80% of the outer perimeter does not contact any element extending higher than the flat upper surface.

For some applications, the tray is transparent. For some applications, the tray is optical grade transparent. For some applications, the tray includes a transparent plastic material.

For some applications, the upper surface has a level of hydrophobicity such that it is configured to contact a drop of water with a contact angle that is between 60 and 120 degrees. For some applications, the upper surface has a level of hydrophobicity such that it is configured to contact a drop of water with a contact angle that is between 75 and 105 degrees.

For some applications, the apparatus is shaped and sized to fit inside a vial having a length of 44 mm and a diameter of 12.5 mm.

For some applications, a vial is provided, and the apparatus is shaped and sized to fit inside the vial. For some applications, the vial includes a cryogenic vial, which includes a material that can withstand temperatures as low as negative 196 degrees Celsius.

For some applications, the apparatus further includes a handle including:
  a first handle portion being generally perpendicular to the tray, and disposed at an end of the tray; and
  a second handle portion being generally parallel to the tray, and coupled to the first handle portion.

For some applications, the first handle portion is disposed at a proximal end of the tray, the tray has a central longitudinal axis that extends through the proximal end and a distal end of the tray, and the central longitudinal axis falls on or is generally parallel to a plane defined by the first handle portion.

For some applications, a thickness of the first handle portion is between 0.3 and 3 mm, and a thickness of the second handle portion is between 0.3 and 3 mm. For some applications, a surface area of the first handle portion is between 20 and 80 mm2, and a surface area of the second handle portion is between 20 and 80 mm2.

For some applications:
  the handle further includes a handle wall coupled to the end of the tray, and
  each of the first handle portion and the second handle portion is:
    generally perpendicular to the handle wall, and
    coupled to the tray, by being coupled to the handle wall.

For some applications, the handle wall is shaped to define one or more slit-shaped openings therethrough. For some applications, the handle wall is shaped to define exactly two slit-shaped openings therethrough.

For some applications, the protrusions are configured to separate the entire underside of the tray from a flat surface on which the tray may be placed.

For some applications:
the underside of the tray provides one or more delineated portions thereof having a shape selected from the group consisting of: a circular shape, an elliptical shape, a square shape, a parallelogram shape, a rhombus shape, a rhomboid shape, and a rectangular shape,
the plurality of protrusions includes one or more groups of one or more delineating protrusions, each group being shaped to delineate one of the delineated portions of the underside of the tray,
each delineated portion of the underside of the tray being delineated by virtue of being contained within a minimum bounding envelope that bounds the group of delineating protrusions that delineates the delineated portion, the envelope having the selected shape, and
the tray is transparent, the transparency of the tray facilitating placement of the fluid on portions of the upper surface that are above the delineated portions of the underside of the tray.

For some applications, at least one of the delineated portions of the underside of the tray has a surface area that is between 1 and 30 mm2. For some applications, at least one of the delineated portions of the underside of the tray has a surface area that is between 10 and 30 mm2. For some applications, a total surface area of the delineated portions of the underside of the tray is between 3 and 90 mm2. For some applications, the total surface area of the delineated portions of the underside of the tray is between 45 and 75 mm2.

For some applications, a total surface area of the delineated portions of the underside of the tray is between 3% and 80% of a surface area of the underside of the tray. For some applications, the total surface area of the delineated portions of the underside of the tray is between 30% and 60% of the surface area of the underside of the tray.

For some applications, at least one of the delineated portions of the underside of the tray has a surface area that is between 1% and 27% of a surface area of the underside of the tray. For some applications, at least one of the delineated portions of the underside of the tray has a surface area that is between 10% and 27% of a surface area of the underside of the tray.

For some applications, the selected shape is the circular shape, and the one or more delineated portions of the underside of the tray have the circular shape. For some applications, each group of delineating protrusions includes a pair of mutually-facing circular-arc-shaped protrusions, the circular-arc-shaped protrusions of each pair having a smallest separation therebetween that is between 0.5 and 2 mm.

For some applications, each group of delineating protrusions includes two or more delineating protrusions that have a smallest separation therebetween that is between 0.5 and 2 mm. For some applications, each group of delineating protrusions includes a pair of mutually-facing delineating protrusions.

For some applications, the selected shape is the rectangular shape, and the one or more delineated portions of the underside of the tray have the rectangular shape. For some applications, the selected shape is the elliptical shape, and the one or more delineated portions of the underside of the tray have the elliptical shape. For some applications, the selected shape is the rhombus shape, and the one or more delineated portions of the underside of the tray have the rhombus shape.

For some applications, the one or more groups of one or more delineating protrusions include fewer than five groups. For some applications, the one or more groups of one or more delineating protrusions include five or more groups.

For some applications, the one or more groups of one or more delineating protrusions are arranged in rows, a number of the rows being selected from the group consisting of: one, two, and three.

For some applications, the plurality of protrusions includes:
supporting protrusions that protrude a first distance from the underside of the tray; and
delineating protrusions that (a) protrude from a portion of the underside of the tray that is farther from a perimeter of the underside of the tray, relative to the supporting protrusions, and (b) protrude a second distance from the underside of the tray that is not greater than the first distance.

For some applications, the second distance is equal to the first distance, the delineating protrusions protruding the second distance.

For some applications, the plurality of protrusions includes at least four supporting protrusions, each of a majority of which is less than 3 mm from a respective corner of the underside of the tray, such that each of the corners of the underside of the tray is within 3 mm of at least one of the supporting protrusions.

For some applications:
the underside of the tray provides one or more delineated portions thereof having a total surface area that is between 3 and 90 mm2,
the plurality of protrusions includes one or more groups of one or more delineating protrusions, each group being shaped to delineate one of the delineated portions of the underside of the tray, and
the tray is transparent, the transparency of the tray facilitating placement of the fluid on portions of the upper surface that are above the delineated portions of the underside of the tray.

For some applications, each of the plurality of protrusions protrudes an equal distance from the underside of the tray.

For some applications, each of the plurality of protrusions protrudes a distance that is between 0.2 and 0.8 mm from the underside of the tray. For some applications, each of the plurality of protrusions protrudes a distance that is between 0.4 and 0.6 mm from the underside of the tray.

For some applications, each of the plurality of protrusions protrudes a distance from the underside of the tray that is between 50% and 150% of the thickness of the tray. For some applications, each of the plurality of protrusions protrudes a distance from the underside of the tray that is between 60% and 110% of the thickness of the tray.

For some applications, a total cross-sectional area of the protrusions that is parallel to the underside of the tray is less than 50 mm2. For some applications, the total cross-sectional area of the protrusions that is parallel to the underside of the tray is between 10 and 25 mm2.

For some applications, a total cross-sectional area of the protrusions that is parallel to the underside of the tray is less than 40% of a surface area of the underside of the tray.

For some applications, the total cross-sectional area of the protrusions that is parallel to the underside of the tray is between 7% and 20% of the surface area of the underside of the tray.

For some applications, the tray is rectangular. For some applications, a length of the tray is between 12 and 25 mm. For some applications, the length of the tray is between 16 and 21 mm. For some applications, a width of the tray is between 3 and 12 mm. For some applications, the width of the tray is between 6 and 9 mm.

For some applications, the flat upper surface is shaped to define an outer perimeter, and the tray can be placed over a drawn rectangle such that at least 90% of the outer perimeter is horizontally separated from a perimeter of the rectangle by less than 1.5 mm.

For some applications, a shape of the tray is selected from the group consisting of: round, circular, square, and elliptical.

For some applications, the tray includes a polycarbonate.

There is further provided, in accordance with an application of the present invention, apparatus for use with a fluid that contains biological cells, the apparatus including:
  a tray shaped to define:
    a flat upper surface configured to support the fluid, the upper surface not being completely surrounded by a wall and having a surface area that is less than 900 mm2, and
    an underside; and
  a handle including:
    a first handle portion being generally perpendicular to the tray, and disposed at an end of the tray; and
    a second handle portion being generally parallel to the tray, and coupled to the first handle portion,
    the tray having a thickness between 0.4 and 0.8 mm.

For some applications, the first handle portion is disposed at a proximal end of the tray, the tray has a central longitudinal axis that extends through the proximal end and a distal end of the tray, and the central longitudinal axis falls on or is generally parallel to a plane defined by the first handle portion.

For some applications, the tray is further shaped to define a plurality of protrusions protruding from the underside of the tray.

For some applications:
  the underside of the tray provides one or more delineated portions thereof having a total surface area that is between 3 and 90 mm2,
  the plurality of protrusions includes one or more groups of one or more delineating protrusions, each group being shaped to delineate one of the delineated portions of the underside of the tray, and
  the tray is transparent, the transparency of the tray facilitates placement of the fluid on portions of the upper surface that are above the delineated portions of the underside of the tray.

For some applications, the protrusions are configured to separate the entire underside of the tray from a flat surface on which the tray may be placed.

For some applications, each of the plurality of protrusions protrudes an equal distance from the underside of the tray.

For some applications, the plurality of protrusions includes:
  supporting protrusions that protrude a first distance from the underside of the tray; and
  delineating protrusions that (a) protrude from a portion of the underside of the tray that is farther from a perimeter of the underside of the tray, relative to the supporting protrusions, and (b) protrude a second distance from the underside of the tray that is not greater than the first distance.

For some applications, the second distance is equal to the first distance, the delineating protrusions protruding the second distance.

For some applications, the plurality of protrusions includes at least four supporting protrusions, each of a majority of which is less than 3 mm from a respective corner of the underside of the tray, such that each of the corners of the underside of the tray is within 3 mm of at least one of the supporting protrusions.

For some applications:
  the underside of the tray provides one or more delineated portions thereof having a shape selected from the group consisting of: a circular shape, an elliptical shape, a square shape, a parallelogram shape, a rhombus shape, a rhomboid shape, and a rectangular shape,
  the plurality of protrusions includes one or more groups of one or more delineating protrusions, each group being shaped to delineate one of the delineated portions of the underside of the tray,
  each delineated portion of the underside of the tray being delineated by virtue of being contained within a minimum bounding envelope that bounds the group of delineating protrusions that delineates the delineated portion, the envelope having the selected shape, and
  the tray is transparent, the transparency of the tray facilitates placement of the fluid on portions of the upper surface that are above the delineated portions of the underside of the tray.

For some applications, the selected shape is the circular shape, and the one or more delineated portions of the underside of the tray have the circular shape. For some applications, each group of delineating protrusions includes a pair of mutually-facing circular-arc-shaped protrusions, the circular-arc-shaped protrusions of each pair having a smallest separation therebetween that is between 0.5 and 2 mm.

For some applications, each group of delineating protrusions includes two or more delineating protrusions that have a smallest separation therebetween that is between 0.5 and 2 mm. For some applications, each group of delineating protrusions includes a pair of mutually-facing delineating protrusions.

For some applications, the selected shape is the elliptical shape, and the one or more delineated portions of the underside of the tray have the elliptical shape. For some applications, the selected shape is the rectangular shape, and the one or more delineated portions of the underside of the tray have the rectangular shape. For some applications, the selected shape is the rhombus shape, and the one or more delineated portions of the underside of the tray have the rhombus shape.

For some applications, the one or more groups of one or more delineating protrusions are arranged in rows, a number of the rows being selected from the group consisting of: one, two, and three.

For some applications, the tray has a property selected from the group consisting of: transparency, and translucency. For some applications, the tray is transparent.

For some applications:
  the flat upper surface is shaped to define an outer perimeter,
  at least some of the outer perimeter does not contact any element extending higher than the flat upper surface, and
  at least some of the outer perimeter contacts an element extending higher than the flat upper surface.

For some applications, the upper surface is configured to contact a drop of the fluid with a contact angle that is between 60 and 120 degrees. For some applications, the upper surface is configured to contact the drop of the fluid with a contact angle that is between 75 and 105 degrees.

For some applications, the tray is rectangular. For some applications, a length of the tray is between 12 and 25 mm. For some applications, the length of the tray is between 16 and 21 mm. For some applications, a width of the tray is between 3 and 12 mm. For some applications, the width of the tray is between 6 and 9 mm.

For some applications, the apparatus is shaped and sized to fit inside a vial having a length of 44 mm and a diameter of 12.5 mm.

For some applications, a vial is provided, and the apparatus is shaped and sized to fit inside the vial. For some applications, the vial includes a cryogenic vial, which includes a material that can withstand temperatures as low as negative 196 degrees Celsius.

For some applications, the tray includes a polycarbonate.

For some applications, the flat upper surface is shaped to define an outer perimeter, and the tray can be placed over a drawn rectangle such that at least 90% of the outer perimeter is horizontally separated from a perimeter of the rectangle by less than 1.5 mm.

For some applications, a shape of the tray is selected from the group consisting of: round, circular, square, and elliptical.

For some applications, a thickness of the first handle portion is between 0.3 and 3 mm, and a thickness of the second handle portion is between 0.3 and 3 mm.

For some applications, a surface area of the first handle portion is between 20 and 80 mm2, and a surface area of the second handle portion is between 20 and 80 mm2.

For some applications:
the handle further includes a handle wall coupled to the end of the tray, and
each of the first handle portion and the second handle portion is:
generally perpendicular to the handle wall, and
coupled to the tray, by being coupled to the handle wall.

For some applications, the handle wall is shaped to define one or more slit-shaped openings therethrough. For some applications, the handle wall is shaped to define exactly two slit-shaped openings therethrough.

There is still further provided, in accordance with an application of the present invention, a method including:
providing apparatus that includes (i) a tray shaped to define (a) a flat upper surface configured to support the fluid, the upper surface not being completely surrounded by a wall and having a surface area that is less than 900 mm2, and (b) an underside, the tray having a thickness between 0.4 and 0.8 mm, and a property selected from the group consisting of: transparency, and translucency, and (ii) a plurality of protrusions protruding from the underside of the tray;
extracting from a subject a fluid that contains biological cells; and
placing droplets of the fluid on the flat upper surface of the tray of the apparatus.

For some applications, the method further includes cryopreserving the droplets of the fluid by placing the apparatus in a freezer.

For some applications, cryopreserving the droplets of the fluid includes inserting the tray into a cryogenic vial.

For some applications,
the apparatus further includes a handle including (a) a first handle portion being generally perpendicular to the tray, and disposed at an end of the tray, and (b) a second handle portion being generally parallel to the tray, and coupled to the first handle portion, and
the method further includes removing the tray from a cryogenic vial by grasping one of the first and the second handle portions.

For some applications, the first handle portion is disposed at a proximal end of the tray, and a plane defined by the first handle portion is generally parallel to a central longitudinal axis of the tray that extends through the proximal end and a distal end of the tray.

For some applications,
the underside of the tray provides one or more delineated portions thereof having a shape selected from the group consisting of: a circular shape, an elliptical shape, a square shape, a parallelogram shape, a rhombus shape, a rhomboid shape, and a rectangular shape,
the plurality of protrusions includes one or more groups of one or more delineating protrusions, each group being shaped to delineate one of the delineated portions of the underside of the tray,
each delineated portion of the underside of the tray being delineated by virtue of being contained within a minimum bounding envelope that bounds the group of delineating protrusions that delineates the delineated portion, the envelope having the selected shape,
the tray is transparent, and
placing the droplets of the fluid on the flat upper surface includes placing the droplets of the fluid on portions of the upper surface that are above the delineated portions of the underside of the tray.

The present invention will be more fully understood from the following detailed description of embodiments thereof, taken together with the drawings, in which:

DETAILED DESCRIPTION OF APPLICATIONS

Figure 1A:
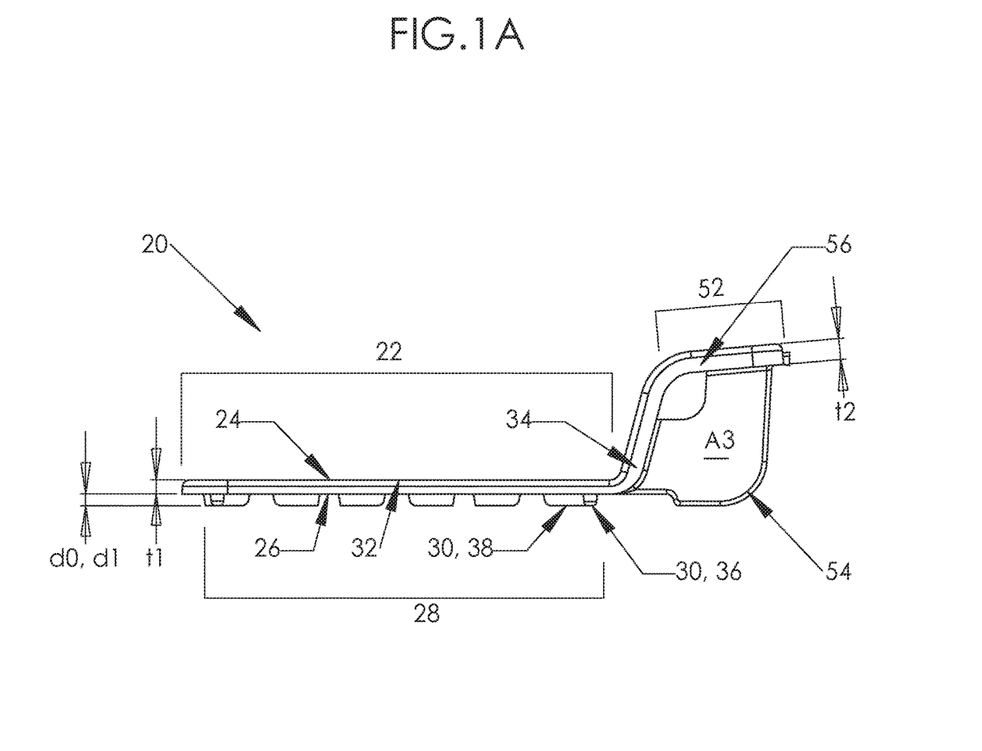
FIGS. 1A-B are schematic illustrations of apparatus for use with a fluid that contains biological cells, in accordance with some applications of the present invention.
Figure 1B:
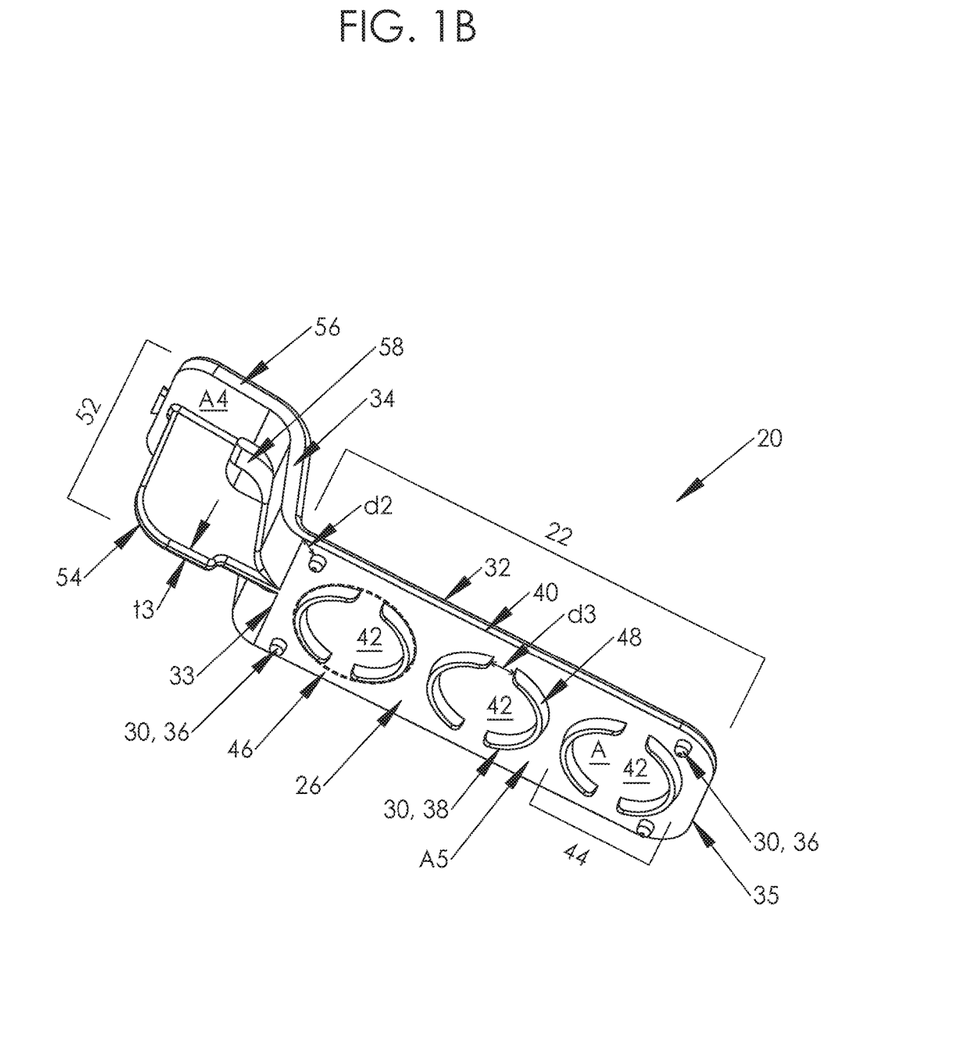

Reference is made to FIGS. 1A-B, which are schematic illustrations of apparatus 20 for use with a fluid that contains biological cells, in accordance with some applications of the present invention. Apparatus 20 comprises a tray 22, which is shaped to define a flat upper surface 24, configured to support the fluid, and an underside 26.

As shown in FIGS. 1A-B, flat upper surface 24 is not completely surrounded by a wall, i.e., at least a portion of the flat upper surface is unwalled. As a result, upper surface 24 is generally more accessible, relative to if it were to be completely surrounded by a wall. For example, the unwalled portions of the flat upper surface are generally more accessible from a lateral direction, relative to if these portions were to be walled. Thus, the at least partial absence of a wall surrounding upper surface 24 facilitates the placement of fluid on the tray, and/or retrieval of fluid from the tray, and/or extraction of cells from the fluid following placement of the fluid on the tray.

Alternatively or additionally to upper surface 24 not being completely surrounded by a wall, upper surface 24 is typically shaped to define an outer perimeter 32, at least some (e.g., at least 20%, 40%, 60%, or 80%) of which does not contact any element extending higher than upper surface 24, and at least some of which contacts an element extending higher than upper surface 24. For example, FIGS. 1A-B show perimeter 32 not contacting any element extending higher than the upper surface, except for along the width of the tray at one of the ends of the tray, where it contacts a handle wall 34, described in more detail hereinbelow. (The end of the tray at which perimeter 32 contacts handle wall 34 is referred to hereinbelow as a proximal end 33 of the tray, while the opposite end is referred to as a distal end 35 of the tray.)

Typically, apparatus 20 further comprises a plurality 28 of protrusions 30 protruding from underside 26. Protrusions 30 are typically configured to separate the entire underside 26 from a flat surface on which the tray may be placed. (For example, as further described hereinbelow, protrusions 30 may be arranged such that each of the corners of underside 26 is near a protrusion, such that no portion of underside 26 touches the surface upon which the tray is placed.) Protrusions 30 generally prevent tray 22 from sticking to a wet surface on which the tray may be placed (e.g., a surface having oil thereon, as further described hereinbelow), by separating underside 26 from the wet surface.

Plurality 28 of protrusions 30 typically comprises two types of protrusions 30. Protrusions of the first type, namely, supporting protrusions 36, protrude a first distance d0 from underside 26, thus generally supporting tray 22 when it is placed on a surface. Protrusions of the second type, namely, delineating protrusions 38, protrude a second distance d1 from the underside of the tray, where d1 is not greater than d0. Delineating protrusions 38 delineate one or more portions of underside 26, as described in more detail hereinbelow. Due to the delineating function of delineating protrusions 38, delineating protrusions 38 typically protrude from a portion of underside 26 that is farther from a perimeter 40 of the underside, relative to supporting protrusions 36. For example, as shown in FIG. 1B, supporting protrusions 36 may be near the corners of the underside, with delineating protrusions 38 being closer to the center of the underside.

In some applications, plurality 28 of protrusions 30 comprises at least four supporting protrusions 36, each of a majority of which is less than 3 mm from a respective corner of the underside. For example, FIG. 1B shows four supporting protrusions 36, each of which is a distance d2 that is less than 3 mm from a respective corner of the underside. (For the rounded corners shown at distal end 35 of the tray in FIG. 1B, a protrusion 36 is considered to be less than 3 mm from the corner if it is less than 3 mm from at least one point on the rounded corner.) Furthermore, in such applications, each of the corners of the underside is within 3 mm of at least one of supporting protrusions 36. Such an arrangement of supporting protrusions 36 typically facilitates effective supporting of tray 22.

Typically, each of plurality 28 of protrusions 30 protrudes a distance d0 or d1 that is at least 0.2 mm, less than 0.8 mm, and/or between 0.2 and 0.8 mm (e.g., between 0.4 and 0.6 mm) from underside 26. Alternatively or additionally, distance d0 or d1 is at least 50%, less than 150%, and/or between 50% and 150% (e.g., between 60% and 110%) of thickness t of the tray. Typically, each of plurality 28 of protrusions 30 protrudes an equal distance from underside 26. In other words, (a) d0 is typically the same for all of supporting protrusions 36, such that tray 22 is parallel to the surface upon which it is placed, and (b) d1 is typically equal to d0, such that delineating protrusions 38 also support tray 22.

In some applications, plurality 28 of protrusions 30 comprises one or more groups 44 of one or more delineating protrusions 38. (For example, FIG. 1B shows three groups 44 of two delineating protrusions 38.) Each group 44 is shaped to delineate a delineated portion 42 of underside 26, such that underside 26 provides one or more delineated portions 42. Each delineated portion 42 is delineated by virtue of being contained within a minimum bounding envelope 46 of a particular shape that bounds the respective group 44, the delineated portion having the same shape as envelope 46. (Minimum bounding envelope 46 is not part of apparatus 20.) For example, in FIG. 1B, circular delineated portions 42 are delineated by virtue of being contained within respective circular envelopes 46 that bound respective groups 44. The shape of delineated portions 42 is typically a circular shape, an elliptical shape, a square shape, a parallelogram shape, a rhombus shape, a rhomboid shape, or a rectangular shape. (Generally, in the context of the claims and specification of the present application, an elliptical shape is a non-circular elliptical shape, unless there is no reference to a circular shape alongside the reference to the elliptical shape. The same applies to other types of shapes referred to herein. For example, a rectangular shape is a non-square rectangular shape, unless there is no reference to a square shape alongside the reference to the rectangular shape.)

The placement of the fluid above delineated portions 42 generally facilitates subsequent retrieval of the fluid and/or extraction of cells from the fluid following placement of the fluid on the tray. For example, in certain IVF techniques, several droplets of seminal fluid from a subject may be placed above delineated portions 42, and tray 22 is subsequently placed in a freezer for cryopreservation of the fluid. Upon removing the tray from the freezer, a technician may wish to retrieve some of the seminal fluid, and/or may wish to extract one or more sperm cells from the seminal fluid. Delineated portions 42 allow the technician to more quickly find the droplets, relative to if the tray did not have the delineated portions. Typically, tray 22 is transparent (e.g., optical grade transparent) or translucent. The transparency or translucency of tray 22 facilitates the use of delineated portions 42. In other words, the transparency or translucency of tray 22 helps the technician place the fluid over the delineated portions, and/or subsequently retrieve the fluid, and/or extract cells from the fluid following placement of the fluid on the tray. Typically, in addition to being transparent or translucent, tray 22 is as smooth and level as possible.

At least some of the properties described above make apparatus 20 particularly useful for use with a fluid that contains a relatively small number of cells, e.g., seminal fluid taken from a subject whose sperm count is relatively low. For example, the transparency or translucency of tray 22 may facilitate the locating of cells for extraction from the fluid, in that the technician may use an optical microscope when attempting to locate the cells. Also, the unwalled portions of upper surface 24 may facilitate the micromanipulation that is typically required to extract the cells from the fluid.

In some applications, tray 22 comprises a plastic material, such as a transparent plastic material and/or a polycarbonate, e.g., a transparent polycarbonate.

In some applications, at least one delineated portion 42 has a surface area A that is at least 1 mm2, less than 30 mm2, and/or between 1 and 30 mm2 (e.g., between 10 and 30 mm2). Alternatively or additionally, at least one delineated portion 42 has a surface area A that is at least 1%, less than 27%, and/or between 1% and 27% (e.g., between 10% and 27%) of a surface area A5 of the underside. In some applications, the total surface area of the delineated portions of the underside is at least 3 mm2, less than 90 mm2, and/or between 3 and 90 mm2 (e.g., between 45 and 75 mm2). Alternatively or additionally, the total surface area of the delineated portions of the underside is at least 3%, less than 80%, and/or between 3% and 80% (e.g., between 30% and 60%) of surface area A5.

In some applications, as shown in FIG. 1B, each group 44 of delineating protrusions 38 comprises two or more delineating protrusions 38 that have a smallest separation d3 therebetween that is at least 0.5 mm, less than 2 mm, and/or between 0.5 and 2 mm. For example, each group 44 of delineating protrusions 38 may comprise a pair of mutually-facing delineating protrusions 38, such as a pair of mutually-facing circular-arc-shaped protrusions 48. Protrusions 48 of each pair have smallest separation d3 therebetween that is at least 0.5 mm, less than 2 mm, and/or between 0.5 and 2 mm. The space (separation d3) between protrusions 48 of each pair generally prevents suction from preventing separation of the tray from a wet (e.g., oily) surface, such as a microscope slide, upon which it may be placed. The seminal fluid must be covered in oil to prevent the rapid evaporation of the seminal fluid.

In general, the scope of the present invention allows for any suitable number of groups 44 of delineating protrusions 38. For example, in some applications, there are fewer than five groups 44 (e.g., three groups 44, as in FIG. 1B), while in other applications, there are five or more groups 44. Groups 44 are typically arranged in one, two, or three rows. (FIG. 1B shows one row of groups 44.)

Figure 2:
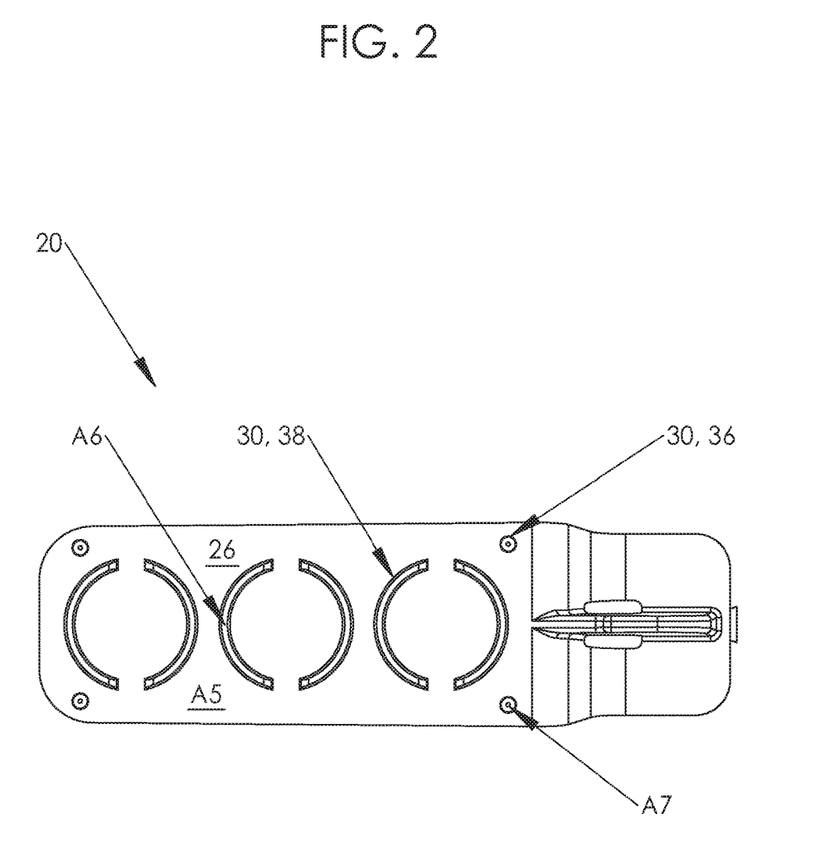
FIG. 2 is a schematic illustration of an underside of the tray of FIGS. 1A-B, in accordance with some applications of the present invention.

Reference is now made to FIG. 2, which is a schematic illustration of underside 26 of tray 22, in accordance with some applications of the present invention. Typically, the total cross-sectional area of protrusions 30 that is parallel to the underside of the tray is less than 50 mm2. For example, the total cross-sectional area of protrusions 30 that is parallel to underside 26 may be at least 10 mm2, less than 25 mm2, and/or between 10 and 25 mm2. (In the example shown in FIG. 2, the total cross-sectional area of protrusions 30 is approximately equal to 6×A6+4×A7.) Alternatively or additionally, the total cross-sectional area of protrusions 30 that is parallel to the underside of the tray may be less than 40% of surface area A5. For example, the total cross-sectional area may be at least 7%, less than 20%, and/or between 7% and 20% of surface area A5.

Figure 3A:
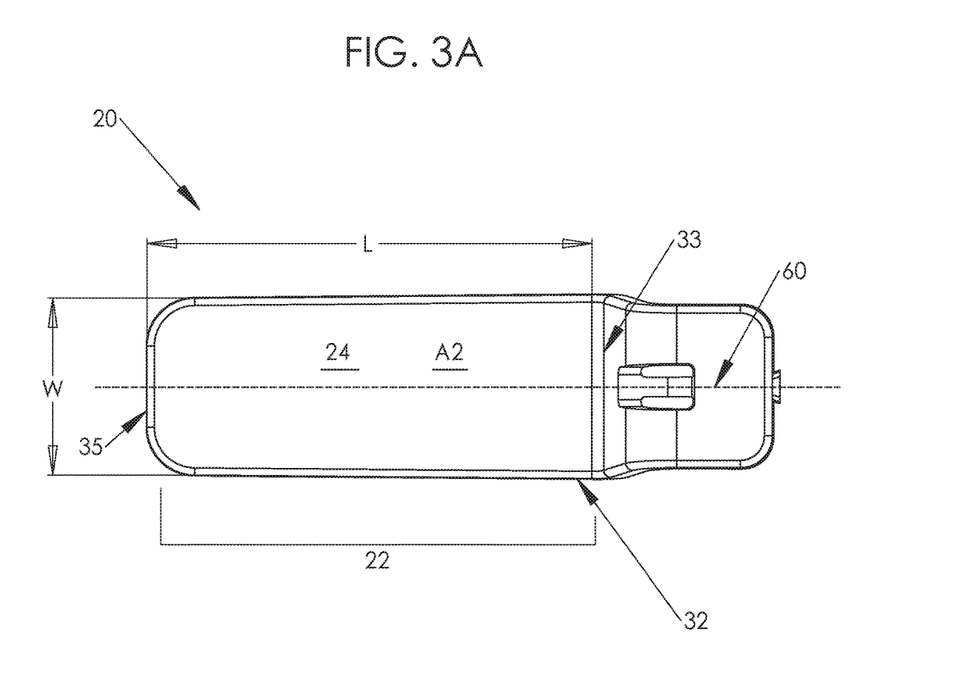
FIGS. 3A-B are schematic illustrations of apparatus for use with a fluid that contains biological cells, in accordance with some applications of the present invention.
Figure 3B:
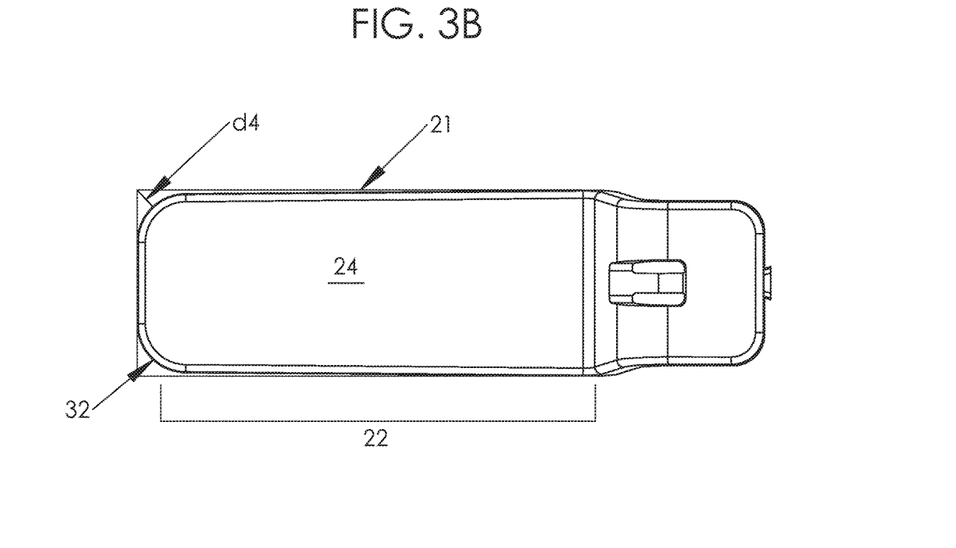

Reference is now made to FIGS. 3A-B, which are schematic illustrations of apparatus 20, in accordance with some applications of the present invention. Typically, as shown in FIGS. 1-3, tray 22 is rectangular. It is noted that tray 22 is considered to be rectangular even if it is not perfectly rectangular, as long as its shape is substantially rectangular. In the context of the present description, "substantially rectangular" means that, as shown in FIG. 3B, tray 22 can be placed over a drawn rectangle 21 such that at least 90% of outer perimeter 32 is horizontally separated from a perimeter of rectangle 21 by a distance d4 that is less than 1.5 mm. A rectangular tray 22 typically has a length L that is at least 12 mm, less than 25 mm, and/or between 12 and 25 mm (e.g., between 16 and 21 mm). A rectangular tray 22 further typically has a width w that is at least 3 mm, less than 12 mm, and/or between 3 and 12 mm (e.g., between 6 and 9 mm).

In some applications, tray 22 is not rectangular, but is instead round, circular, square, or elliptical. Tray 22 typically has a thickness t (FIG. 1A) between 0.4 and 0.8 mm, and upper surface 24 typically has a surface area A2 that is less than 900 mm2.

Reference is again made to FIGS. 1A-B. Typically, apparatus 20 further comprises a handle 52. Handle 52 comprises a first handle portion 54, which is generally perpendicular to tray 22 (e.g., defines a plane that defines an angle of at least 75 degrees, such as at least 80 degrees, with a plane defined by the tray), and is disposed at proximal end 33 of the tray. Handle 52 further comprises a second handle portion 56, which is generally parallel to tray 22 (e.g., defines a plane that defines an angle of less than 15 degrees, such as less than 10 degrees, with a plane defined by the tray), and is coupled to first handle portion 54. Tray 22 has a central longitudinal axis 60 (labeled in FIG. 3A) that extends through proximal and distal ends 33 and 35 of tray 22. Typically, central longitudinal axis 60 falls on or is generally parallel to a plane defined by first handle portion 54 (e.g., defines an angle of at least 75 degrees, such as at least 80 degrees, with the plane).

Handle 52 generally facilitates the handling of tray 22, in that, by virtue of the respective orientations of first handle portion 54 and second handle portion 56, it may be grasped (e.g., using tweezers) from a number of different directions. This convenient handling may be particularly helpful when inserting and removing apparatus 20 from a vial, as described hereinbelow with reference to FIGS. 5A-B.

Typically, handle 52 further comprises handle wall 34, which is coupled to proximal end 33 of tray 22. As shown in FIGS. 1A-B, each of first handle portion 54 and second handle portion 56 is generally perpendicular to handle wall 34 (e.g., defines a plane that defines an angle of at least 75 degrees, such as at least 80 degrees, with a plane defined by handle wall 34), and is coupled to tray 22 by being coupled to handle wall 34.

Typically, handle wall 34 is shaped to define one or more (e.g., exactly two) slit-shaped openings 58 therethrough. Following the placement of the fluid on tray 22, tray 22 is typically placed on an oil-covered surface, in order that a layer of oil should cover the fluid and thus prevent the evaporation thereof. Slit-shaped opening(s) 58 generally prevent oil from being trapped underneath the tray, by allowing the oil to flow onto the tray from underneath the tray, thus helping tray 22 remain in a stable upright position on the oil-covered surface.

In some applications, both the thickness t2 of first handle portion 54 and the thickness t3 of second handle portion 56 are at least 0.3 mm, less than 3 mm, and/or between 0.3 and 3 mm. In some applications, both the surface area A3 of first handle portion 54 and the surface area A4 of second handle portion 56 are at least 20 mm2, not greater than 80 mm2, and/or between 20 and 80 mm2. (Surface areas A3 and A4 include all of the exposed areas of the respective handle portions.)

Figure 4:
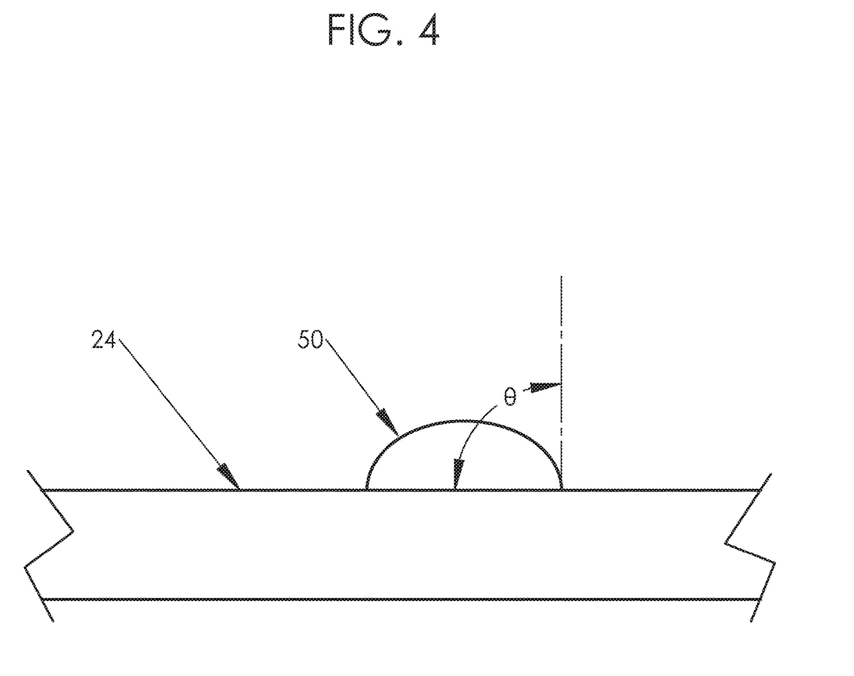
FIG. 4 is a schematic illustration of a portion of apparatus for use with a fluid that contains biological cells, in accordance with some applications of the present invention.

Reference is now made to FIG. 4, which is a schematic illustration of a portion of apparatus 20, in accordance with some applications of the present invention. In some applications, upper surface 24 has a level of hydrophobicity such that it is configured to contact a drop of water 50 with a contact angle theta that is at least 60 degrees, less than 120 degrees, and/or between 60 and 120 degrees (e.g., between 75 and 105 degrees). This level of hydrophobicity is generally sufficient for droplets of fluid placed on the upper surface to maintain their shape to a certain extent (thus facilitating retrieval of the fluid and/or extraction of cells from the fluid), but is low enough such that the fluid adheres to the upper surface.

Figure 5A:
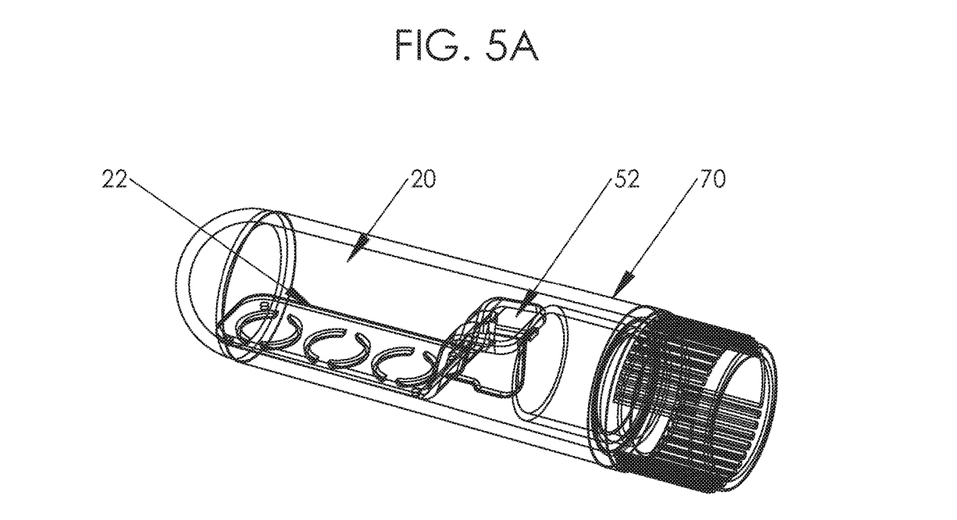
FIGS. 5A-B are schematic illustrations of the apparatus of FIGS. 1A-B inserted into a vial, in accordance with some applications of the present invention.
Figure 5B:
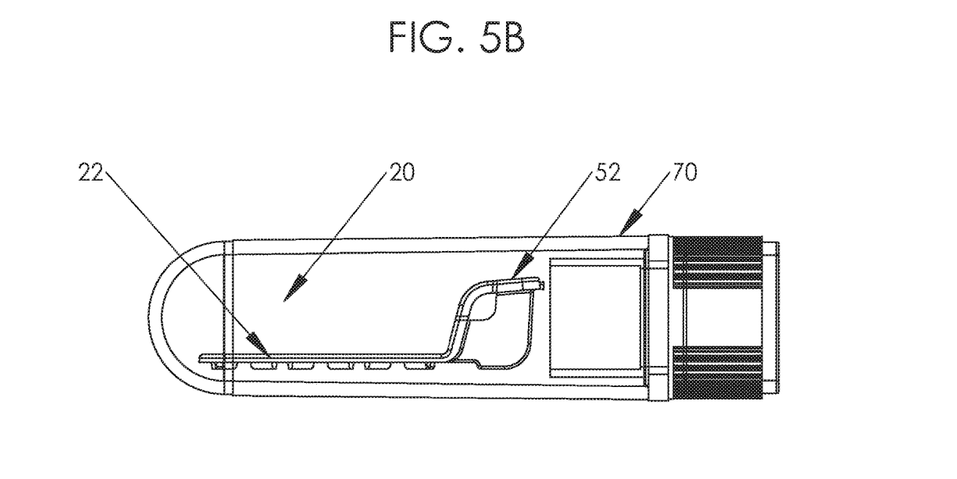

Reference is now made to FIGS. 5A-B, which are schematic illustrations of apparatus 20 inserted into a vial 70, in accordance with some applications of the present invention. Typically, apparatus 20 (including tray 22 and handle 52) fits inside a standard-sized vial that is used for storage (e.g., cryopreservation) of the fluid, i.e., a cryogenic vial. Typically, cryogenic vial 70 comprises a material (e.g., polypropylene) that can withstand temperatures as low as negative 196 degrees Celsius. Typically, cryogenic vial 70 is sterile. Apparatus 20 is shaped and sized to fit inside vial 70. For example, in some applications, apparatus 20 (including tray 22 and handle 52) is shaped and sized to fit inside a vial having a length of 44 mm and a diameter of 12.5 mm. For example, cryogenic vial 70 may comprise a commercially-available NUNC® CRYOTUBE® manufactured by Sigma-Aldrich (Saint Louis, Mo., USA).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a fluid that contains biological cells, the apparatus comprising:
   a tray shaped to define:
      a flat upper surface configured to support the fluid, the upper surface not being completely surrounded by a wall and having a surface area that is less than 900 mm$^2$, and an underside; and
      a plurality of protrusions protruding from the underside of the tray,
         the tray having a thickness that is between 0.4 and 0.8 mm,
            wherein the underside of the tray provides one or more delineated portions thereof having a shape selected from the group consisting of: a circular shape, an elliptical shape, a square shape, a parallelogram shape, a rhombus shape, a rhomboid shape, and a rectangular shape, wherein the plurality of protrusions comprises one or more groups of one or more delineating protrusions, each group being shaped to delineate one of the delineated portions of the underside of the tray, each delineated portion of the underside of the tray being delineated by virtue of being contained within a minimum bounding envelope that bounds the group of delineating protrusions that delineates the delineated portion, the envelope having the selected shape, and
wherein the tray is transparent, the transparency of the tray facilitating placement of the fluid on portions of the upper surface that are above the delineated portions of the underside of the tray; and
   a handle comprising: a first handle portion being generally perpendicular to the tray, and disposed at an end of the tray; and a second handle portion being generally parallel to the tray, and coupled to the first handle portion.

2. The apparatus according to claim 1, wherein:
   the flat upper surface is shaped to define an outer perimeter,
   at least some of the outer perimeter does not contact any element extending higher than the flat upper surface, and
   at least some of the outer perimeter contacts an element extending higher than the flat upper surface.

3. The apparatus according to claim 2, wherein at least 40% of the outer perimeter does not contact any element extending higher than the flat upper surface.

4. The apparatus according to claim 2, wherein at least 60% of the outer perimeter does not contact any element extending higher than the flat upper surface.

5. The apparatus according to claim 1, wherein the apparatus is shaped and sized to fit inside a vial having a length of 44 mm and a diameter of 12.5 mm.

6. The apparatus according to claim 1, wherein a thickness of the first handle portion is between 0.3 and 3 mm, and a thickness of the second handle portion is between 0.3 and 3 mm.

7. The apparatus according to claim 1, wherein a surface area of the first handle portion is between 20 and 80 mm$^2$, and a surface area of the second handle portion is between 20 and 80 mm$^2$.

8. The apparatus according to claim 1, wherein at least one of the delineated portions of the underside of the tray has a surface area that is between 10 and 30 mm$^2$.

9. The apparatus according to claim 1, wherein the total surface area of the delineated portions of the underside of the tray is between 30% and 60% of the surface area of the underside of the tray.

10. The apparatus according to claim 1, wherein the underside of the tray provides one or more delineated portions thereof having a total surface area that is between 3 and 90 mm$^2$.

11. A method comprising:
   providing the apparatus according to claim 1;
   extracting from a subject the fluid that contains biological cells; and
   placing droplets of the fluid on the flat upper surface of the tray of the apparatus.

12. The method according to claim 11, further comprises removing the tray from a cryogenic vial by grasping one of the first and the second handle portions.

13. The method according to claim 11, wherein placing the droplets of the fluid on the flat upper surface comprises placing the droplets of the fluid on portions of the upper surface that are above the delineated portions of the underside of the tray.

* * * * *